(12) United States Patent
Wang

(10) Patent No.: US 7,052,651 B2
(45) Date of Patent: May 30, 2006

(54) DISPOSABLE IMMUNOASSAY SAMPLE-COLLECTOR AND CHROMATOGRAPHIC-TESTING DEVICE

(75) Inventor: Naishu Wang, Poway, CA (US)

(73) Assignee: Alfa Scientific Designs, Inc., Poway, CA (US)

( * ) Notice: Subject to any disclaimer, the term of this patent is extended or adjusted under 35 U.S.C. 154(b) by 180 days.

(21) Appl. No.: 10/765,405

(22) Filed: Jan. 26, 2004

(65) Prior Publication Data

US 2005/0163660 A1   Jul. 28, 2005

(51) Int. Cl.
*G01N 21/78* (2006.01)
(52) U.S. Cl. .......................................... 422/58; 422/61
(58) Field of Classification Search .................. 422/58, 422/61
See application file for complete search history.

(56) References Cited

U.S. PATENT DOCUMENTS

2003/0022392 A1*  1/2003  Hudak ......................... 436/518
2003/0206829 A1*  11/2003  Cui et al. ..................... 422/58

* cited by examiner

*Primary Examiner*—Jill Warden
*Assistant Examiner*—Natalia Levkovich
(74) *Attorney, Agent, or Firm*—Charmasson, Buchaca & Leach, LLP

(57) ABSTRACT

A disposable liquid specimen collector and testing device can be manipulated to distribute a quantified portion of a liquid specimen to separate chromatographic strip-mounting testing stations while shielding the remainder of the specimen from cross-contamination by the immunoassay reagents present in the testing strips. In the resting state, the device exposes the testing station to a desiccant. A separate test station provides for a quick revelation of any adulterating component in the sample specimen. The geometry of the test station and fluid distribution channels assures isobaric conditions throughout the testing areas.

5 Claims, 5 Drawing Sheets

DISPOSABLE IMMUNOASSAY SAMPLE-COLLECTOR AND CHROMATOGRAPHIC-TESTING DEVICE

FIELD OF THE INVENTION

This invention relates to chromatographic immunoassay testing devices and more particularly to apparatuses for collecting a liquid sample and performing concurrent multiple tests by contact with chromatographic strips.

BACKGROUND OF THE INVENTION

The collection of fluid specimens such as blood, saliva and urine and the conduct of immunoassay tests on such specimens to detect the presence or absence of certain chemicals, hormones, antibodies or antigens by dipping into the fluid specimen chromatographic testing strips requires a great deal of manipulation involving risks of contamination, mishandling, mislabeling and even complete loss of the specimen through spilling. Lack of consistency in the volume and pressure conditions of each test can affect the results and distort statistical data gathered from multiplicity of tests. Proper or equal dosage of the specimen, pretesting for adulterating additions further increase the risk of mishandling, contamination and loss. Further, fecal material suspended in a fluid wash buffer, and fluids such as saliva previously diluted in a mouthwash such as a phosphate buffer saliva (PBS) solution would be placed in a separate container prior to testing for hepatitis, HIV and other pathogens, or pathogenic antigens.

This invention results from an attempt to devise a simple, multi-use apparatus that minimizes handling of the specimen while expediting the whole procedure.

SUMMARY OF THE INVENTION

The principal and secondary objects of this invention are to provide an apparatus for safely and accurately conducting a number of immunoassay tests on a quantified amount of a liquid sample by exposure to a number of chromatographic strips while at the same time avoiding contamination or any loss of the sample through inadvertent spilling, in which the apparatus's simplicity and low manufacturing cost of the appartus allow it to be discarded after use.

These and other valuable objects are achieved by a liquid sample collector and polychromatice testing apparatus which comprises a sealable collection vessel associated and integrally formed with a number of testing stations in a single compact, simple, inexpensive and disposable package. A valve manipulable by a knob on the front of the apparatus simultaneously distributes metered amounts of the fluid specimen to a number of testing stations including an adulteration testing station. During pre-use storage and pre and post collection transportation of the apparatus, all the testing areas are exposed to a desiccant compound which is automatically removed before the testing strips are exposed to the test sample. Isobaric conditions are maintained through those testing areas by isometric configuration of all the specimen-carrying structures.

DESCRIPTION OF THE PREFERRED EMBODIMENT OF THE INVENTION

Figure 1:
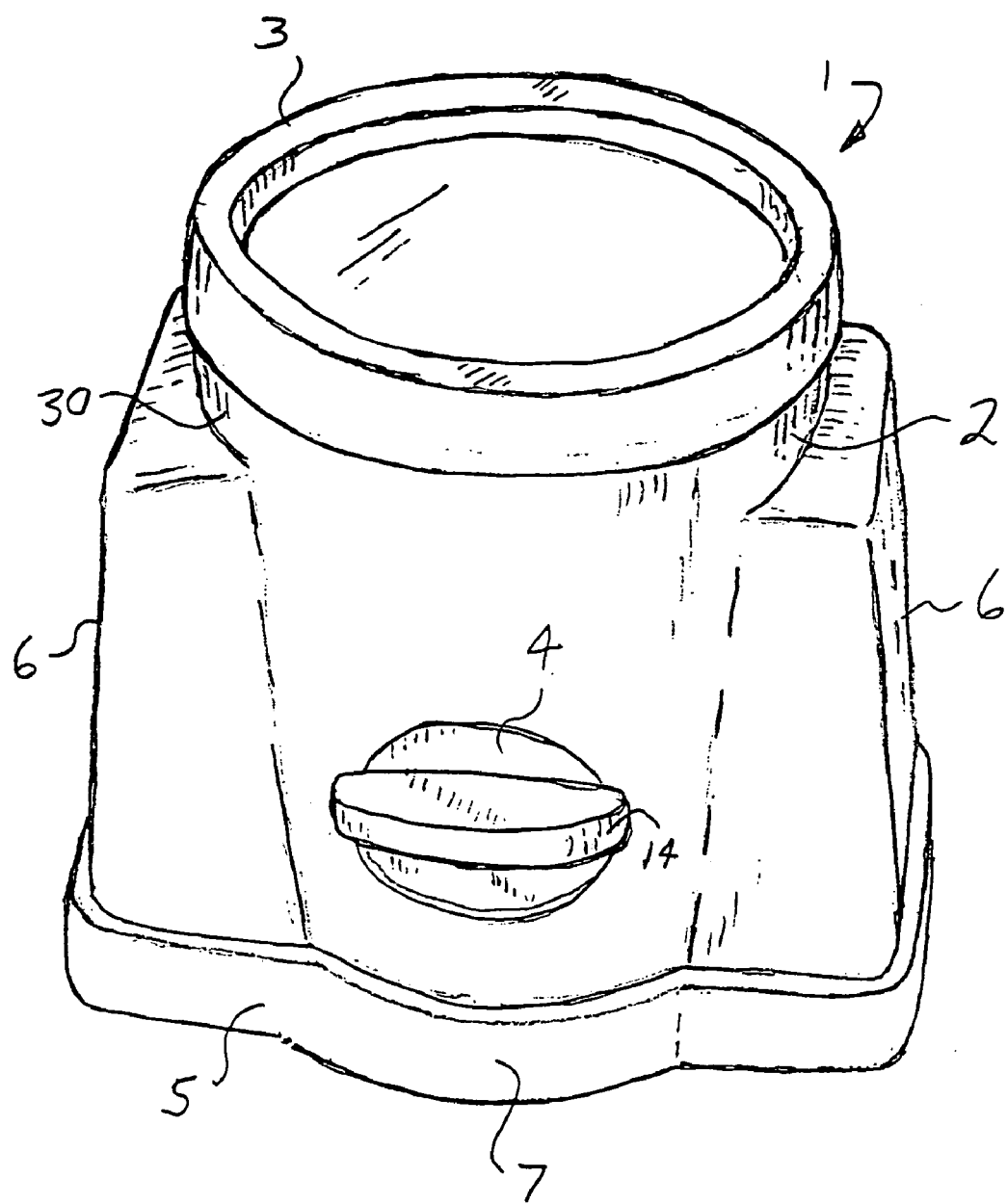
FIG. 1 is a front and top perspective view of the apparatus according to the invention.

Referring now to the drawing, there is shown a disposable and one-time use apparatus 1 for collecting a liquid specimen and conducting a multiplicity of immunochromatographic tests on a metered amount of the specimen.

The apparatus comprises a cylindrical specimen-collecting vessel 2 covered by a self-snapping lid 3, a hand-operable valve 4, a base pan 5, a pair of multi-strip test stations 6 mounted astride the vessel and valve, and an adulteration test station 7 along the frontal edge of the pan 5. The valve 4 is located between the vessel 2 and the pan 5 under a semi-cylindrical tunnel 8 formed in the bottom piece 9 of the vessel. The valve comprises a cylindrical body 10 having an axis X–X' oriented horizontally under a median portion of the vessel 2. The valve is supported by a hemi-cylindrical trough 11 which, with the tunnel portion 8 of the bottom piece, forms a cylindrical bearing 12 into which the cylindrical body 10 of the valve is journaled. An aperture 13 in the tunnel portion of the vessel's bottom piece 9 is controlled by the valve 4.

Figure 3:
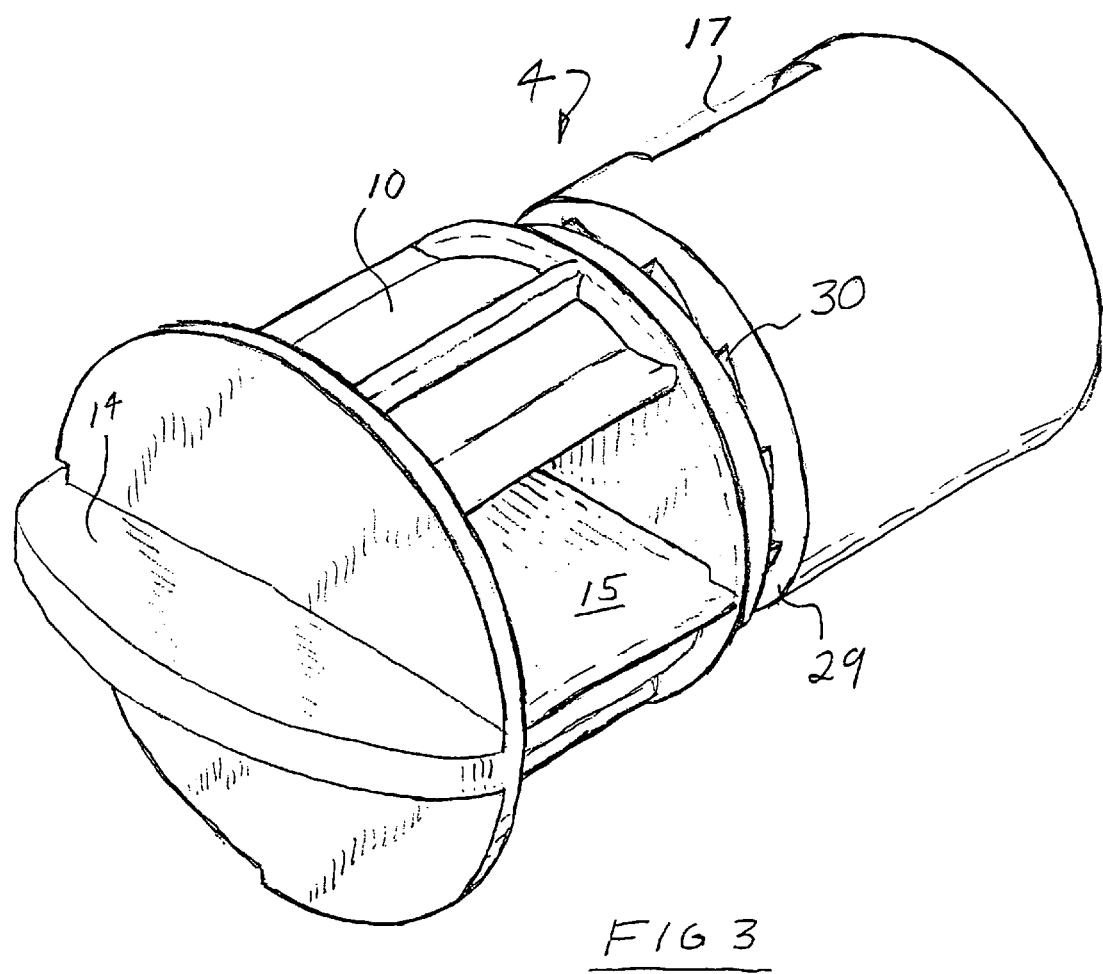
FIG. 3 is a perspective view of the valve body.
Figure 4:
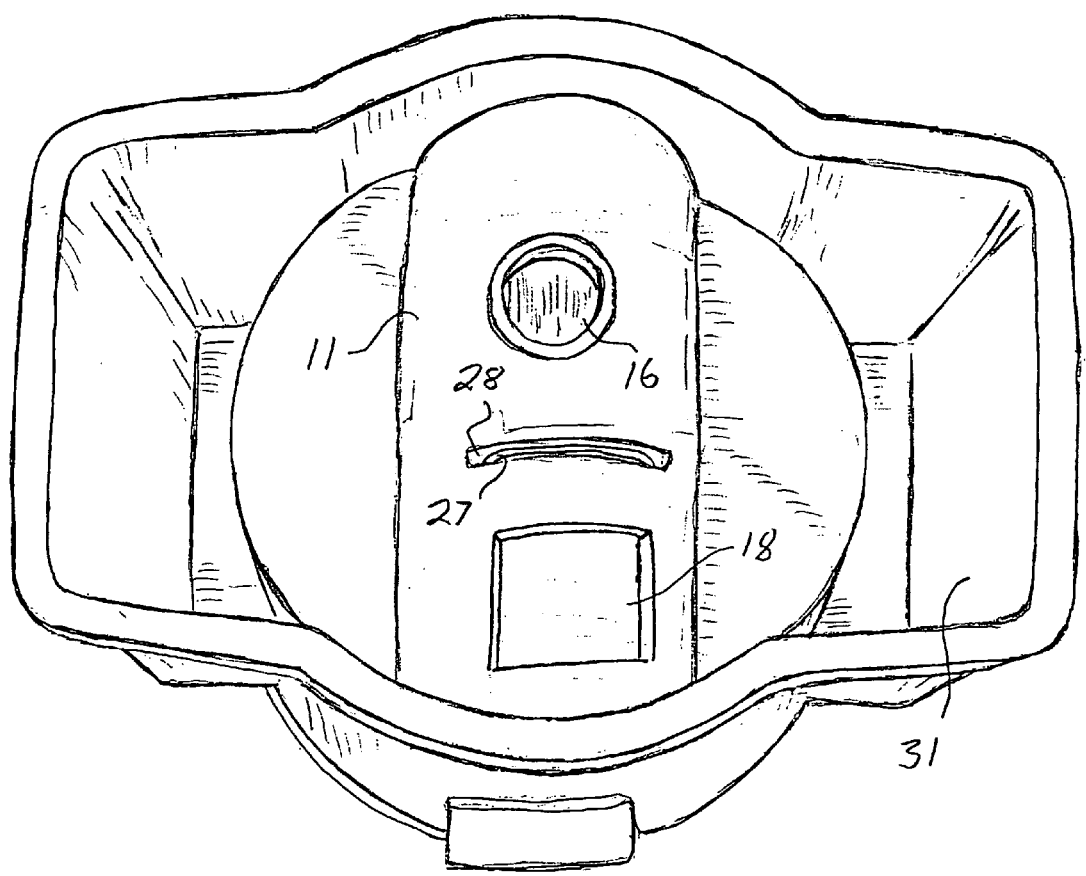
FIG. 4 is a bottom plan view of the apparatus with the base pan removed.

As more specifically illustrated in FIG. 3, the valve comprises a frontal knob 14 for manually controlling the axial rotation of the cylindrical body 10. A lateral first cavity 15 in the cylindrical body of the valve is shaped, positioned and dimensioned to accept a metered amount of fluid specimen through the aperture 13 when, in a first position of the valve, the cavity 15 is lined up with the aperture 13. When the valve is rotated 180 degrees clockwise, the contents of the first cavity 15 is dumped into the underlying pan 5 through a dumping circular port 16 in the bottom of the trough 11. A lateral second cavity 17 is formed into the distal portion of the cylindrical body 10 and positioned axially distant and diameterically opposite the first cavity 15. The second cavity is shaped, dimensioned, and positioned to hold an amount of desiccant which is exposed to the inside surfaces of the underlying pan 5 when the valve is in its first resting position through a second port 18 in the trough section 11. When the valve is rotated to its second dumping position, the second cavity 17 is no longer lined up with the second port 18, and the internal surfaces of the pan are no longer exposed to it.

It should be understood that other types of valve geometry could also be used. For instance, the valve can be of an axially translating type where the knob is held in its most recessed, distal position during storage and shipping. It can be pulled outwardly to an intermediary position where a measured amount of fluid specimen is accepted ito the valve body. Finally, when the knob is pulled in a third most outward position, the measured amount of specimen is dumped into the well 20 through appropriate openings.

Figure 5:
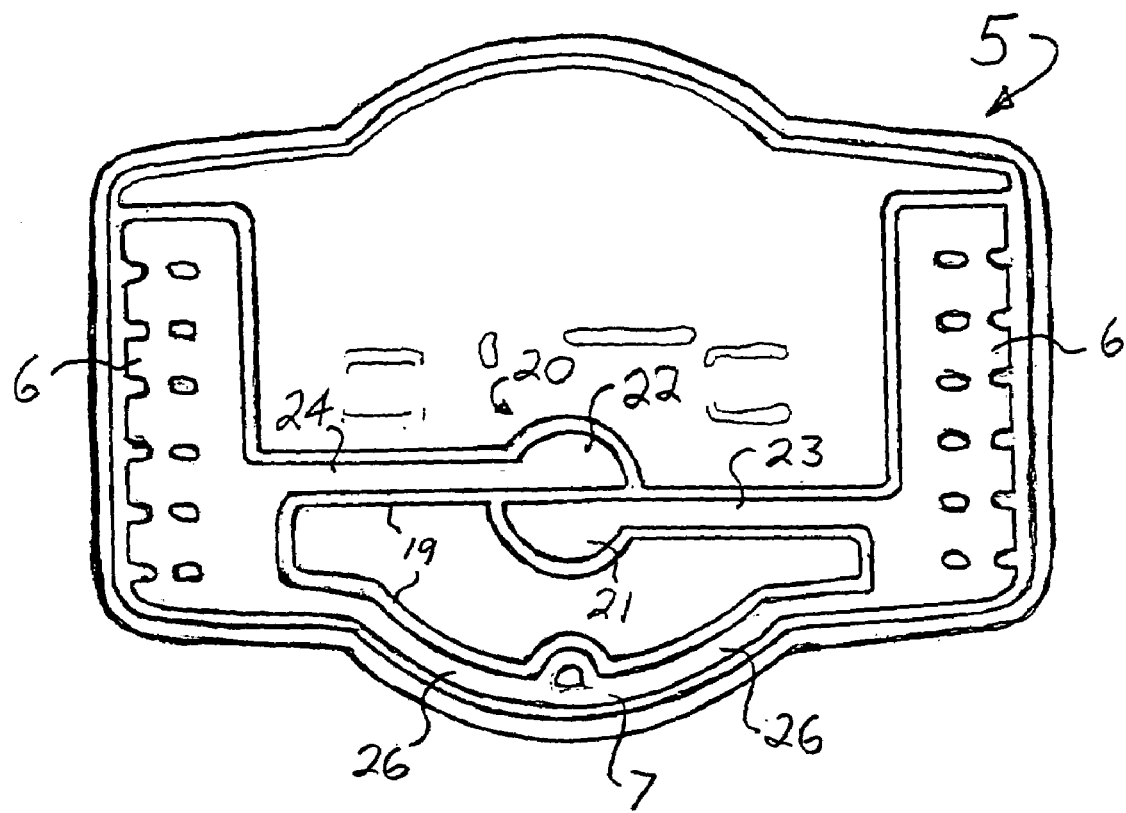
FIG. 5 is a top plan view of the base pan.

As more specifically illustrated in FIG. 5, the inside of the pan is divided by a series of walls 19 to form a cylindrical well 20 commensurate with, and located immediately below the specimen dumping port 16. The well acts as a receiving station for the fluid specimen and is divided into two symmetrical portions 21, 22 each in communication with a passageway 23, 24 leading to the base of one of the testing stations 6. The symmetricality of the well portions, and passageways provides for an isovolumetric and isobaric distribution of the fluid specimen to the pair of testing stations.

Figure 2:
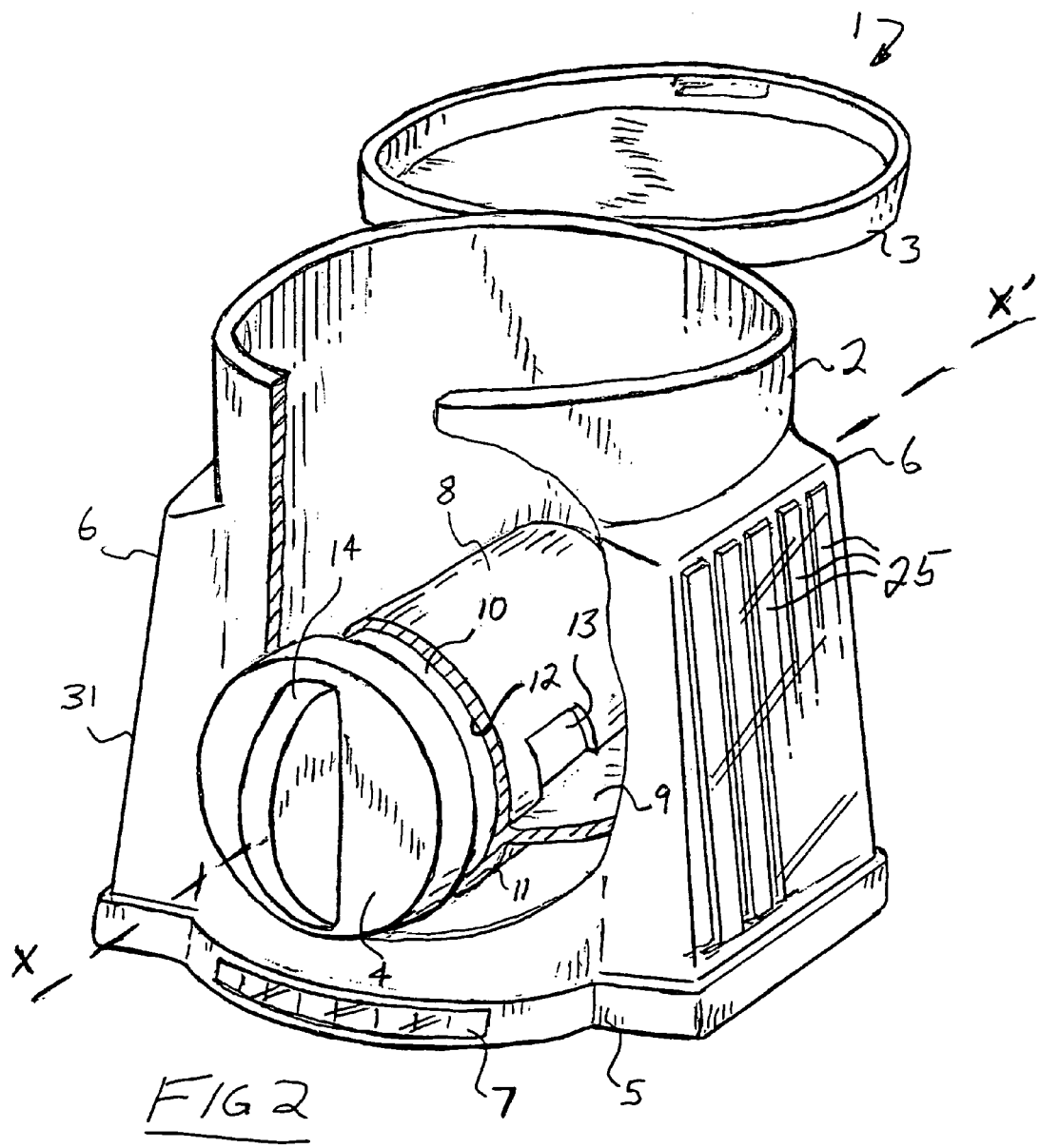
FIG. 2 is a cutout view thereof exposing a portion of the valve mechanism.

As more specifically illustrated in FIG. 2, each of the two lateral testing stations 6 mounts a number of chromatographic testing strips 25 which extend all the way down into the portion of the pan underlying the test station. A pair of symmetrical channels 26 in the frontal portion of the pan diverts an equal amount of fluid specimen from each of the passageways 23, 24 and bring them to the adulteration testing station 7 in the frontal portion of the base pan 5. The symmetricality of the channels 26 preserves the isobaric conditions of the amount of fluid specimen send to the lateral testing stations.

The valve secured into the cylindrical housing 12 by the C-clip 27 engage through a slot 28 in the bottom of the housing and capturing a circular groove 29 in the cylindrical body of the valve between the proximal portion carrying the first cavity 15 and the distal portion carrying the second cavity 17. Engaged into the same groove, is a spring-biased ratchet mechanism 30 which allows only uni-directional, clockwise rotation of the valve, and includes a barrier to prevent travel beyond the 180 degrees necessary to transport the fluid from the vessel to the receiving station in the pan. The external surface of the vessel's wall 31 extends over the lateral test stations 6, 7 to form an all-encompassing transparent shell which meets and is hermetically sealed, with the bottom edges of the pan 5.

Accordingly, there is provided a sealable vessel for collecting an immunoassay liquid specimen that is integrally associated with multi-strip chromatographic testing stations wherein a metered amount of the fluid specimen can be conveniently transported by manipulation of the valve knob to the base pan 5 for distribution to the stations. The pan, valve housing and station walls form a closed chamber which prior to the manipulation of the valve, is exposed to the desiccant to prevent accumulation of moisture into the test station during the storage, and pre and post collection transportation of the apparatus.

While the preferred embodiment of the invention has been described, modifications can be made and other embodiments may be devised without departing from the spirit of the invention and the scope of the appended claims.

What is claimed is:

1. An apparatus for exposing a metered amount of liquid specimen to immunochromatographic test strips, which comprises:
    a base pan;
    a fluid specimen collecting vessel held above said pan;
    said vessel including a vertical wall and a bottom piece having an aperture;
    a distribution valve mounted between said vessel and pan, said valve having a first cavity and being shaped and dimensioned to, in a first position, admit a metered sampling of fluid from said vessel through said aperture into said first cavity, and, in a second position, dump said sampling into said pan;
    a pair of test stations each shaped and dimensioned to hold a chromatographic test device above a portion of said pan and in contact with said sampling;
    wherein said pan comprises a liquid-receiving section under said valve, said section being divided into symmetrical portions each having one of first and second passageways,
    said portions being shaped and positioned to accept isovolumetric amounts of said sampling fluid through said aperture when said valve is placed in said second position;
    said valve further comprises a second cavity containing a desiccant compound, said second cavity having an opening positioned for exposing said pan to said desiccant compound when said valve is placed in said first position.

2. The apparatus of claim 1 which further comprises a control station shaped and positioned to hold a chromatographic device above a portion of said pan and in contact with said sampling, said control station having two symmetrical channels, a first one of said channels leading to said first one passageway and a second one of said channels leading to said second passageway.

3. The apparatus of claim 1, wherein said valve comprises:
    a cylindrical body having an axis oriented horizontally under a median portion of said vessel;
    said cylindrical body having said first cavity shaped and positioned to admit said sampling through said aperture when said valve is in said first position;
    means for rotating said cylindrical body about said axis to expose said first cavity to said pan through said aperture when the valve is in said second position.

4. The apparatus of claim 3, wherein said second cavity is axially distant and diametrically opposite said first cavity.

5. The apparatus of claim 1 which further comprises means for maintaining said sampling into said chamber under isobaric condition.

* * * * *